(12) United States Patent
Ho et al.

(10) Patent No.: US 9,404,847 B2
(45) Date of Patent: *Aug. 2, 2016

(54) METHODS FOR MITIGATING FOULING OF PROCESS EQUIPMENT

(75) Inventors: Teh C. Ho, Bridgewater, NJ (US); Glen B. Brons, Phillipsburg, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 1265 days.

This patent is subject to a terminal disclaimer.

(21) Appl. No.: 13/294,300

(22) Filed: Nov. 11, 2011

(65) Prior Publication Data

US 2012/0118794 A1    May 17, 2012

Related U.S. Application Data

(60) Provisional application No. 61/414,669, filed on Nov. 17, 2010.

(51) Int. Cl.
*C10G 75/04* (2006.01)
*G01N 17/00* (2006.01)
*G01N 25/18* (2006.01)
*C10G 75/00* (2006.01)

(52) U.S. Cl.
CPC .............. *G01N 17/008* (2013.01); *C10G 75/00* (2013.01); *C10G 75/04* (2013.01); *G01N 25/18* (2013.01); *C10G 2300/1033* (2013.01); *C10G 2300/202* (2013.01); *C10G 2300/205* (2013.01); *C10G 2300/4075* (2013.01)

(58) Field of Classification Search
CPC ...................................................... C10G 75/04
See application file for complete search history.

(56) References Cited

U.S. PATENT DOCUMENTS

| 4,766,553 | A | 8/1988 | Kaya et al. |
| 5,871,634 | A | 2/1999 | Wiehe et al. |
| 5,997,723 | A | 12/1999 | Wiehe et al. |
| 2010/0122939 | A1 | 5/2010 | Bauer et al. |
| 2010/0163461 | A1 | 7/2010 | Wright et al. |

FOREIGN PATENT DOCUMENTS

| FR | 2885694 | 11/2006 |
| WO | 0007000 | 2/2000 |

OTHER PUBLICATIONS

Search Report, PCT/US2011/060943, mailed Mar. 23, 2012.
Written Opinion, PCT/US2011/060943, mailed Mar. 23, 2012.

*Primary Examiner* — Manuel Rivera Vargas
(74) *Attorney, Agent, or Firm* — Glenn T. Barrett; Andrew T. Ward

(57) ABSTRACT

Methods for determining the fouling propensity of a hydrocarbon stream and for reducing fouling are provided. In one method, the fouling propensity of a hydrocarbon stream is determined by obtaining a parameter indicative of the fouling propensity by a regression of a series of temperature measurements data for the hydrocarbon stream exiting a test unit. In another method, an effective minimal amount of an antifoulant is added to a hydrocarbon stream to reduce fouling, where the amount of the antifoulant is determined based on the fouling propensity of the hydrocarbon stream.

11 Claims, 10 Drawing Sheets

METHODS FOR MITIGATING FOULING OF PROCESS EQUIPMENT

CROSS REFERENCE TO RELATED APPLICATION

This application relates and claims priority to U.S. Provisional Patent Application No. 61/414,669, entitled "Methods for Mitigating Fouling of Process Equipment" filed on Nov. 17, 2010.

FIELD OF THE INVENTION

The presently disclosed subject matter relates to methods for determining fouling propensity of hydrocarbon streams, as well as for reducing and mitigating fouling of process equipment by the hydrocarbon streams. The method for determining fouling propensity is especially useful in connection with the selection, blending and purchase of hydrocarbon streams for purposes of reducing and mitigating fouling of process equipment.

BACKGROUND

The deposition of organic and/or inorganic foulants on process equipment accounts for a significant amount of energy loss in oil production, refining and chemicals manufacturing. For example, the thermal processing of crude oils, boiling-point fractions, and blends in heat transfer equipment, such as heat exchangers, is hampered by the deposition of insoluble asphaltenes and other contaminants (i.e., particulates, salts, etc.) that may be found in crude oils. Further, the asphaltenes and other organics may thermally degrade to coke when exposed to high heater tube surface temperatures.

Fouling in heat exchangers receiving hydrocarbon process streams can result from a number of mechanisms including chemical reactions, corrosion, deposit of existing insoluble impurities in the stream, and deposit of materials rendered insoluble by the temperature difference between the process stream and the heat exchanger wall. For example, naturally-occurring asphaltenes can precipitate from the crude oil process stream, thermally degrade to form a coke and adhere to the hot surfaces. Further, the high temperature difference found in heat transfer operations result in high surface or skin temperatures when the process stream is introduced to the heater tube surfaces, which contributes to the precipitation of insoluble particulates. Another common cause of fouling is attributable to the presence of salts, particulates and impurities (e.g. inorganic contaminants) found in the crude oil stream. For example, iron oxide/sulfide, calcium carbonate, silica, sodium chloride and calcium chloride have all been found to attach directly to the surface of a fouled heater rod and throughout the coke deposit. These solids promote and/or enable additional fouling of crude oils. The fouling propensities of different hydrocarbon streams (such as crude oils or refinery process streams) may vary considerably. Under the same operating conditions, some streams foul easily, while other streams may experience minimal fouling.

The buildup of insoluble deposits in heat transfer equipment creates an unwanted insulating effect and reduces the heat transfer efficiency. Fouling also reduces the cross-sectional area of process equipment, which decreases flow rates and desired pressure differentials to provide less than optimal operation. As a result, heat transfer equipment are ordinarily taken offline and cleaned either mechanically or chemically, resulting in lost production time. In many cases, fouling even causes unwanted and unexpected shutdowns.

Great strides have been made to develop antifoulant agents, additives or coatings. While the addition of antifoulant additives leads to significant energy savings, it introduces attendant costs, including the cost of the additive itself and the cost of removing the additive from the process downstream. As such, it is vitally important to minimize the amount of additive that is introduced to the process while achieving the desired level of fouling reduction, i.e., using only the minimally required level of additive to achieve effective fouling prevention. This requires the development of an accurate and sensitive way of a priori prediction of the fouling propensity of an oil so that an optimal dosage of the additive can be estimated and applied. As well, the fouling propensity can be used as a basis for selecting, purchasing, and blending various hydrocarbon streams to achieve effective fouling prevention.

SUMMARY OF THE INVENTION

In one aspect of the disclosed subject matter, a method for determining the propensity of a hydrocarbon stream to foul a process equipment is provided. The method includes: (a) introducing a hydrocarbon stream to a test unit, the test unit comprising a chamber defined by a wall for the hydrocarbon to flow through, an inlet for feeding the hydrocarbon into the chamber, an outlet for discharging the hydrocarbon stream, and a heating element maintained at a substantially constant surface temperature Tc and disposed within the chamber for heating the hydrocarbon flowing across the surface of the heating element to cause fouling; (b) obtaining a series of temperature measurements over time of the hydrocarbon stream exiting the outlet of the test unit, including: measuring an initial temperature $T_1$ of the hydrocarbon exiting from the outlet when the heating element is substantially free from fouling; measuring the temperature T(t) of the hydrocarbon exiting from the outlet successively at predetermined time intervals subsequent to measuring the initial temperature $T_1$, where t denotes time; and (c) determining a parameter indicative of the propensity of the hydrocarbon to foul a process equipment by a regression of $\Delta T(t)$ according to the function:

$$\Delta T(t) = 1 - \left[ \frac{1 + k(ut/L - 1)}{(1-k)(1 + kut/L)} \right]^{1/(kq)}$$

where $\Delta T(t)$ is a time dependent quantity which is defined as $\Delta T(t) = [T(t) - T_1]/(T_c - T_1)$, k is the fouling parameter to be determined, t is time, u is the average velocity of the hydrocarbon in the chamber of the test unit, and q is a factor relating to heat transfer of the system comprising the test unit wall, the heating element, and the hydrocarbon stream.

Based on the above-described method for determining the propensity of a hydrocarbon stream, the disclosed subject matter also provides a method for reducing fouling of a hydrocarbon stream. The method includes (a) obtaining a parameter indicative of the propensity of the hydrocarbon to cause fouling; (b) determining an effective minimal amount of an antifoulant relative to the amount of hydrocarbon to be processed based on the parameter obtained; and (c) adding the determined amount of the antifoulant to the hydrocarbon to reduce fouling. Additionally, the determined fouling propensities may be used in connection with a method of reducing fouling in process equipment by selecting appropriate hydrocarbon streams based upon the determined fouling propensity to reduce or avoid fouling by selecting materials with a lower propensity to foul. Furthermore, one or more streams may be selected for purposes of blending the hydrocarbon streams in order to reduce fouling of the process equipment. The selection of the blend aims to yield the lowest overall FSI or FPI for the blend as a whole. The determined fouling propensity can be used in connection with the selection and/or purchase of hydrocarbon streams such that the streams or blends of streams with a low propensity to foul may be employed in process equipment.

In another aspect of the disclosed subject matter, a further method for reducing fouling of a hydrocarbon stream is provided. This method includes: (a) obtaining a parameter indicative of the propensity of the hydrocarbon to cause fouling by relating the following factors: (1) NHI, (2) $S_{BN}$; (3) $I_N$; (4) [Metals], and (5) [N] using a mathematical formula, wherein NHI is the concentration of normal heptane insolubles of the hydrocarbon stream, $S_{BN}$ is the solubility blending number of the hydrocarbon stream, $I_N$ is the insolubility number of the hydrocarbon stream, [Metals] is the total concentration of Ni and V combined in the hydrocarbon stream, and [N] is the total concentration of basic nitrogen of the hydrocarbon stream; (b) determining an effective minimal amount of an antifoulant relative to the amount of hydrocarbon to be processed based on the parameter obtained; and (c) adding the determined amount of the antifoulant to the hydrocarbon to reduce fouling. In one embodiment of this method, the parameter indicative of propensity of a hydrocarbon to foul a process equipment is fouling propensity index (FPI), and the mathematical formula is defined as $$FPI = 2.4 + \frac{NHI}{S_{BN} - I_N} - \{(S_{BN} - I_N) + 1.2 \cdot [Metals] + [N]\}$$

The FPI may be used in connection with the method of reducing fouling in process equipment by selecting appropriate hydrocarbon streams with suitable FPIs. The FPIs may also be used to determine whether or not one or more streams may be selected for purposes of blending the hydrocarbon streams in order to reduce fouling of the process equipment. Further, the FPI can be used in connection with the selection and purchase of hydrocarbon streams such that the streams or blends of streams with a low propensity to foul may be employed in process equipment.

DETAILED DESCRIPTION

In accordance with one aspect of the present invention, a method is provided for determining the propensity of a hydrocarbon stream to foul a process equipment. In one aspect of the disclosed subject matter, a method for determining the propensity of a hydrocarbon stream to foul a process equipment is provided. The method includes: (a) introducing a hydrocarbon stream to a test unit, the test unit comprising a chamber defined by a wall for the hydrocarbon to flow through, an inlet for feeding the hydrocarbon into the chamber, an outlet for discharging the hydrocarbon stream, and a heating element maintained at a substantially constant surface temperature Tc and disposed within the chamber for heating the hydrocarbon flowing across the surface of the heating element to cause fouling; (b) obtaining a series of temperature measurements over time of the hydrocarbon stream exiting the outlet of the test unit, including: measuring an initial temperature $T_1$ of the hydrocarbon exiting from the outlet when the heating element is essentially free from fouling; measuring the temperature profile T(t) of the hydrocarbon exiting from the outlet successively at predetermined time intervals subsequent to measuring the initial temperature $T_1$, where t denotes time; and (c) determining a parameter indicative of the propensity of the hydrocarbon to foul a process equipment by a regression of $\Delta T(t)$ according to the following equation $$\Delta T(t) = 1 - \left[\frac{1 + k(ut/L - 1)}{(1-k)(1 + kut/L)}\right]^{1/(kq)}$$

in which $\Delta T(t)$ is a time dependent quantity which is defined as $\Delta T(t) = (T(t) - T_1)/(T_c - T_1)$, k is the fouling parameter to be determined, which is also referred to as Fouling Susceptibility Index, or FSI, t is time, u is the average velocity of the hydrocarbon in the chamber of the test unit, and q is a factor relating to heat transfer capacity of the system comprising the test unit wall, the heating element, and the hydrocarbon stream.

Figure 1:
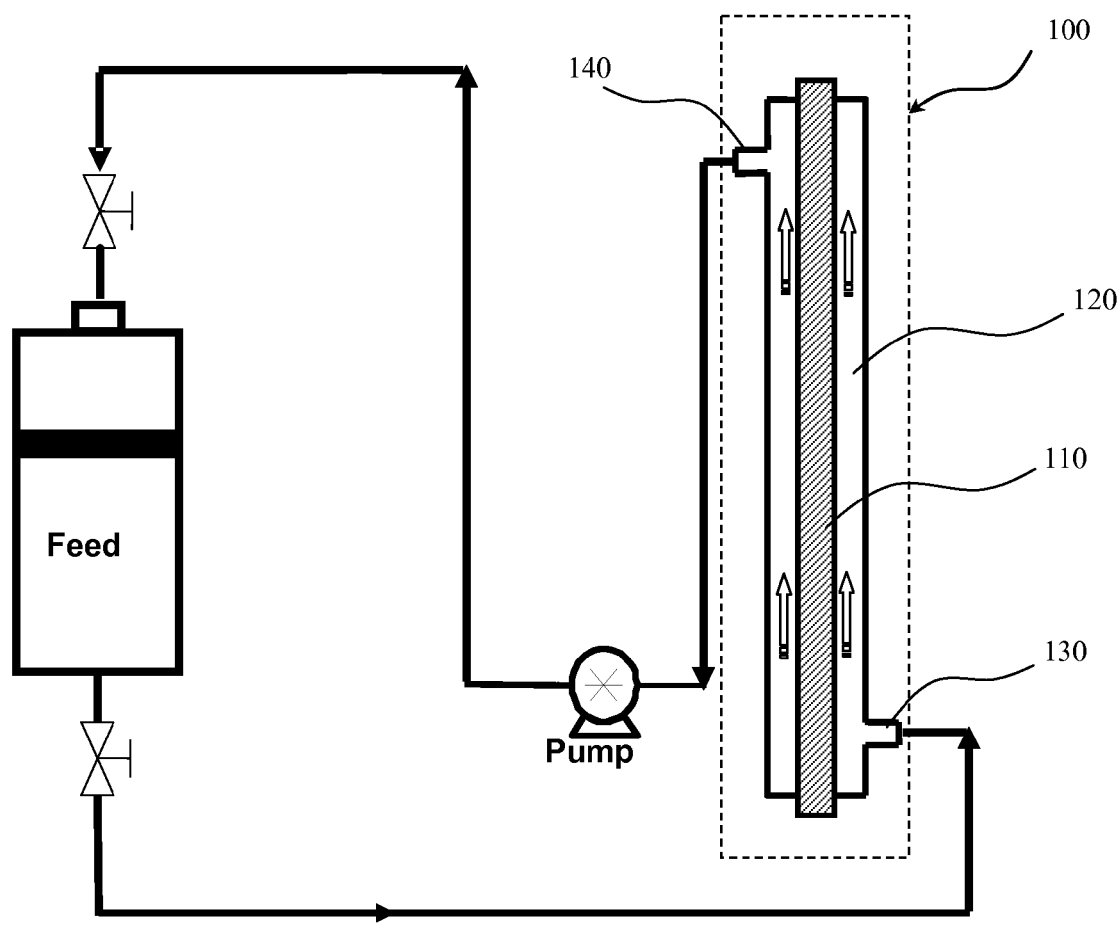
FIG. 1 depicts an exemplary design of a test unit used according to a first aspect of the presently disclosed subject matter.
Figure 2:
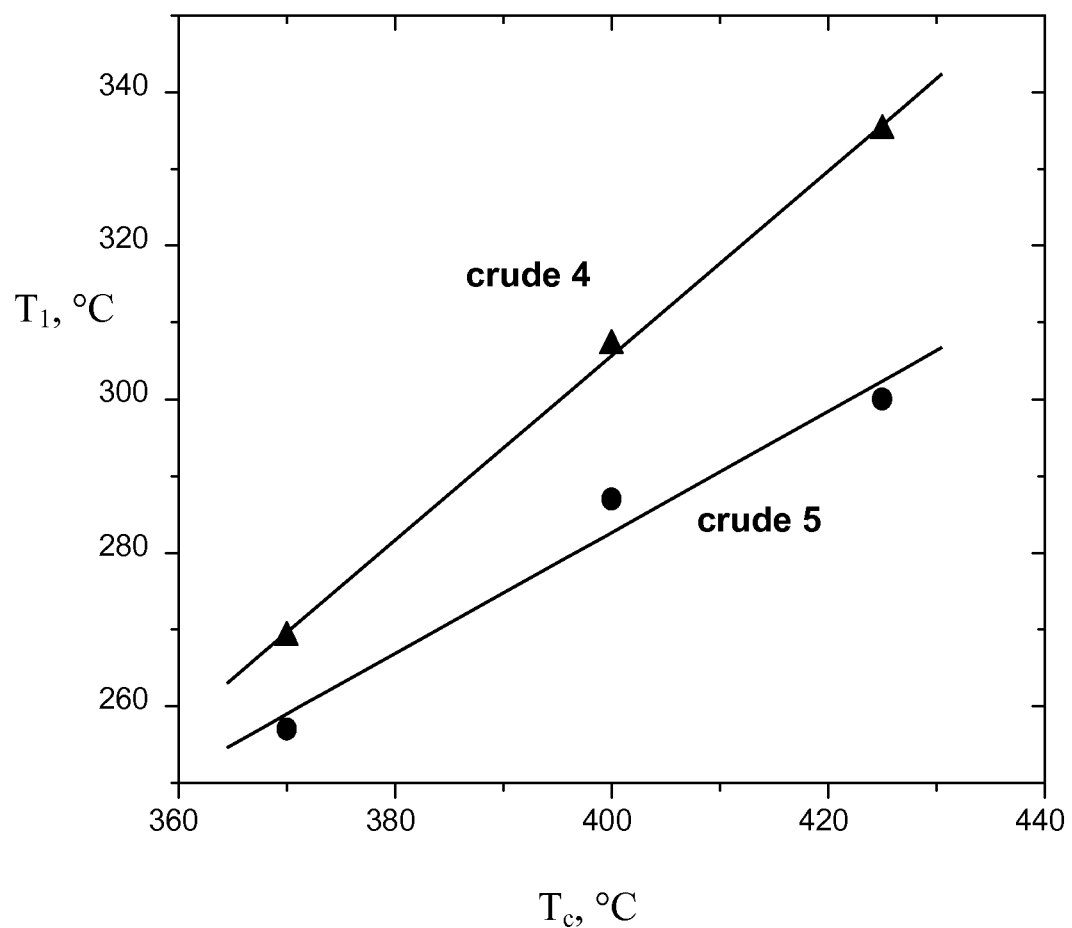
FIG. 2 is a graph illustrating a substantially linear relation between the initial temperature of the effluent hydrocarbon stream exiting from the test unit (when the heated element of the test unit is free of fouling) and the surface temperature of the heated element, according to a first aspect of the presently disclosed subject matter.
Figure 3:
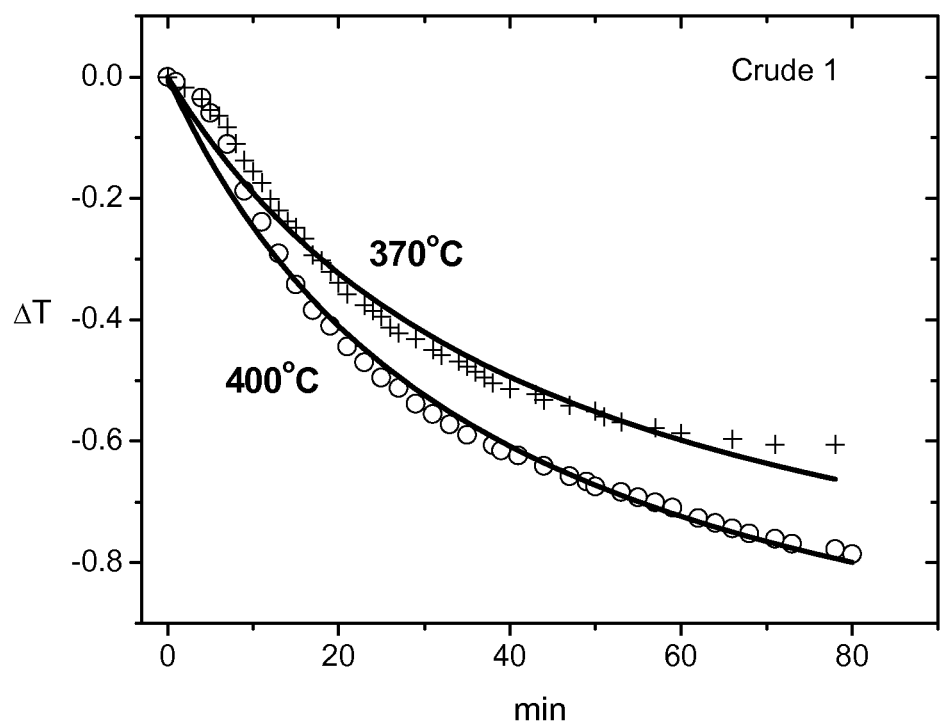
FIG. 3 is a graph displaying a regression of a time dependant function for determining the fouling propensity of a hydrocarbon stream of Crude 1 according to a first aspect of the presently disclosed subject matter.
Figure 4:
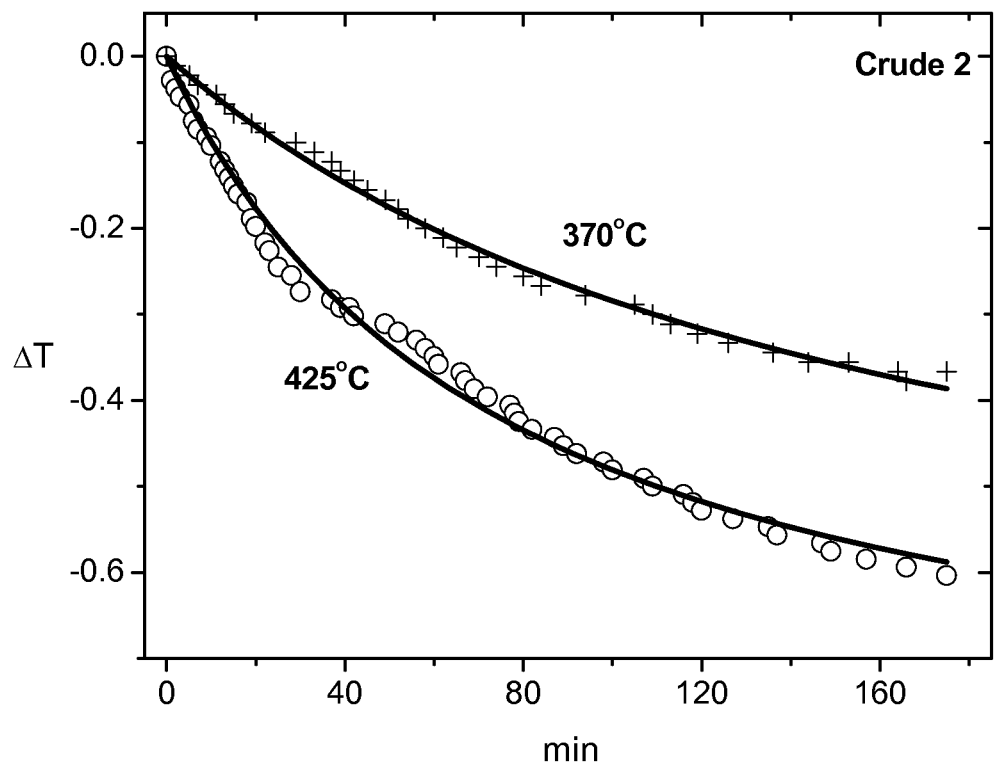
FIG. 4 is a graph displaying a regression of a time dependant function for determining the fouling propensity of a hydrocarbon stream of Crude 2 according to a first aspect of the presently disclosed subject matter.
Figure 5:
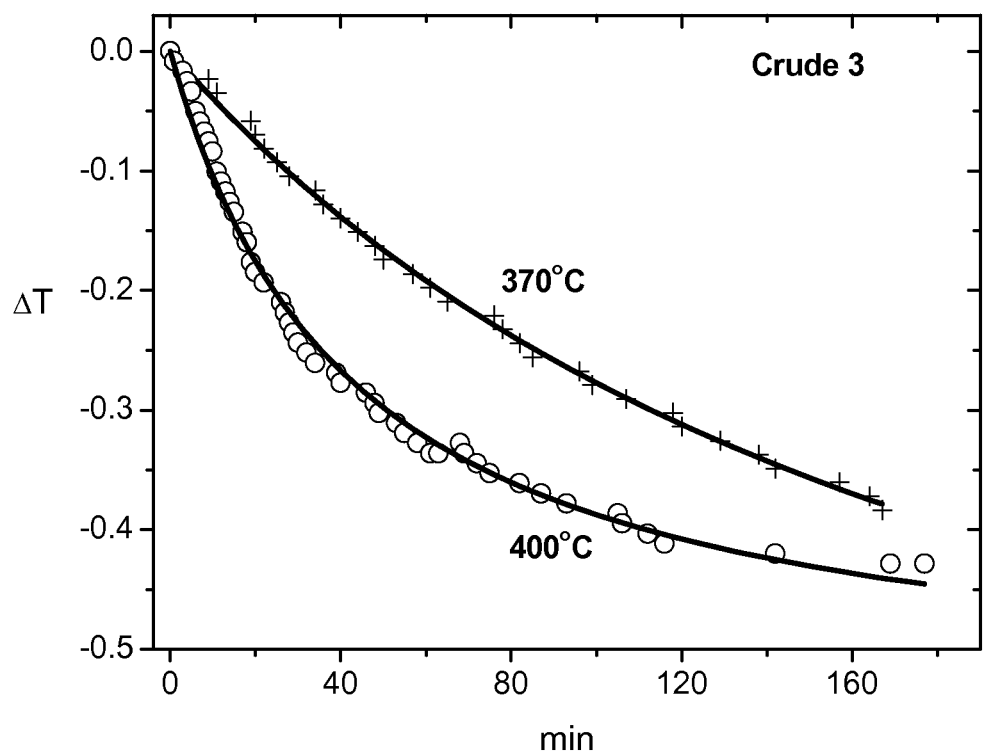
FIG. 5 is a graph displaying a regression of a time dependant function for determining the fouling propensity of a hydrocarbon stream of Crude 3 according to a first aspect of the presently disclosed subject matter.
Figure 6:
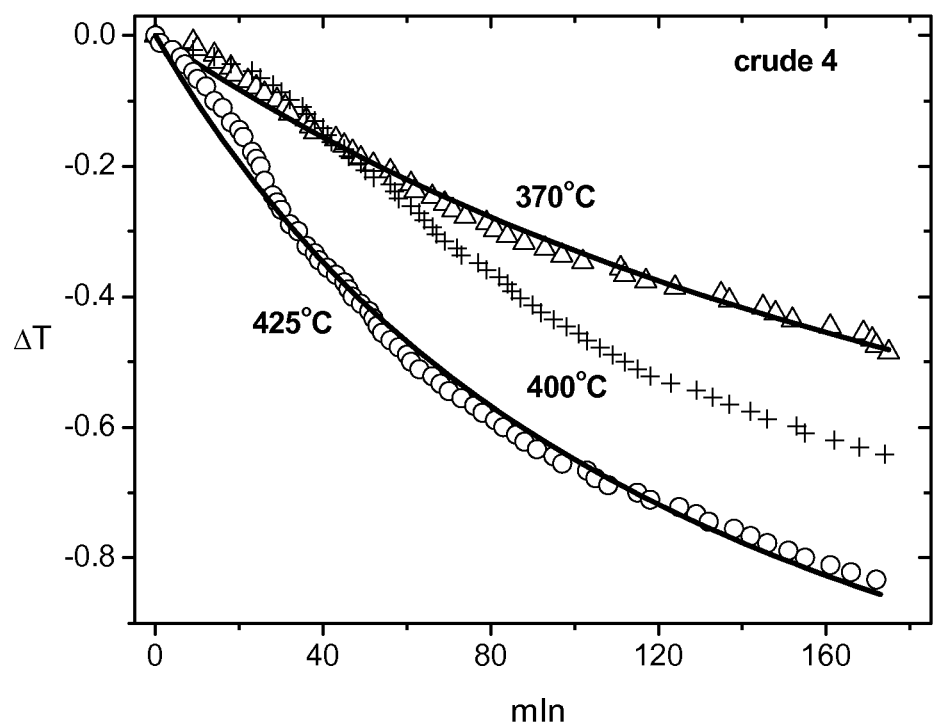
FIG. 6 is a graph displaying a regression of a time dependant function for determining the fouling propensity of a hydrocarbon stream of Crude 4 according to a first aspect of the presently disclosed subject matter.
Figure 7:
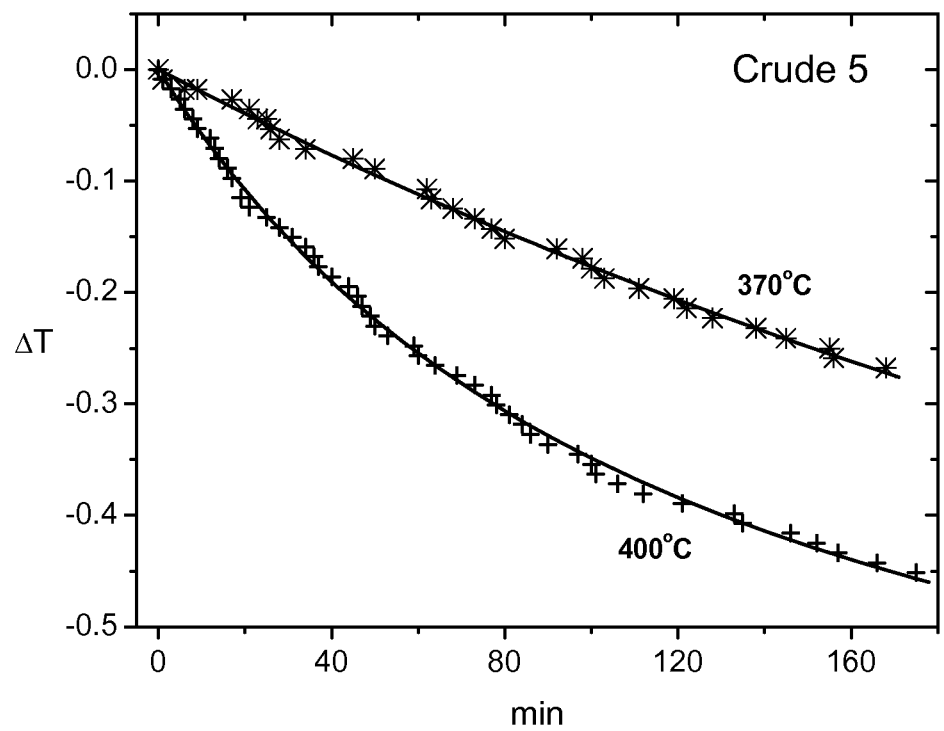
FIG. 7 is a graph displaying a regression of a time dependant function for determining the fouling propensity of a hydrocarbon stream of Crude 5 according to a first aspect of the presently disclosed subject matter.

For purpose of illustration, reference is made to a test unit suitable for determining the fouling propensity of a hydrocarbon stream that involves conducting a series of temperature measurements of said hydrocarbon stream exiting from the test unit. One example of such a test unit is an Alcor Hot Liquid Process Simulator (HPLS) commonly used in the oil industry. The Alcor HPLS has been commonly used for measuring the fouling behavior of oils. As depicted in FIG. 1, the test unit 100 includes a heated rod 110, a tubular chamber 120, an inlet 130 and an outlet 140 disposed at opposing ends of the tubular chamber 120. A hydrocarbon stream can be introduced to the chamber at a constant feed temperature and flow rate into the inlet, flows through the chamber and across the surface of the heated rod which is maintained at a substantially constant surface temperature Tc, and then exits the chamber via the outlet 140. The feed temperature of the hydrocarbon can be in the range of 100-150° C., and are typically lower than the rod temperature which is ranged from about 300° C. to 500° C. Heat is transferred from the rod (which simulates a heat exchanger) to the hydrocarbon stream (e.g., a crude oil or oil blend). As evidenced by FIG. 2, there is a linear relationship between $T_1$ and $T_c$.

As a result of fouling on the surface of the heated rod, the liquid effluent temperature drops over time because the heat transfer efficiency from the rod to the hydrocarbon stream gradually decreases.

To quantify the effect or the severity of the fouling, a series of temperature measurements can be made as hydrocarbon stream exits the test unit. In the presently disclosed subject matter, the entire profile of the temperature versus time is considered, and employed to extract a fouling parameter, i.e., FSI, based on data regression with a specific mathematical formula. A series of successive temperature measurements can be taken subsequent the measurement of $T_1$. A normalized (hence dimensionless) temporal temperature is defined as $$\Delta T(t) = (T(t) - T_1)/(T_c - T_1) \quad (1)$$

As described herein, this temporal data $\Delta T(t)$ is then regressed to obtain a single parameter that reflects the intrinsic fouling propensity of the hydrocarbon stream in question. Specifically, $\Delta T(t)$ can be described by the following function:

$$\Delta T(t) = 1 - \left[\frac{1 + k(ut/L - 1)}{(1-k)(1 + kut/L)}\right]^{1/(kq)} \quad (2)$$

where the dimensionless parameter k is the FSI, which plays the pivotal role in controlling the shape of the $\Delta T(t)$ function, u and L are the average velocity of the hydrocarbon stream and the length of the section of the chamber where the hydrocarbon is heated, respectively. The dimensionless parameter q carries the information on system's heat transfer capacity. Through regression of the $\Delta T(t)$ function, both parameters k and q can be extracted simultaneously. For a group of similar hydrocarbons (e.g., crude oils), the thus-determined k can be used to quantitatively rank the fouling tendency of the oils.

Based on its role in Eq. 2, the greater the FSI for a hydrocarbon indicates a greater likelihood that the hydrocarbon will cause fouling in the process equipment over time. Therefore, hydrocarbons have higher FSI's will require the use of a greater amount of an anti-fouling additive for effective reduction or avoidance of fouling. The quantitative relationship between the FSI (or FPI, described below) and the required anti-foulant additive dosage is dependent on the kind of anti-foulant used and the operating conditions of the process equipment.

In accordance with another aspect of the present invention, a method is provided for determining the propensity of a hydrocarbon to foul process equipment, which does not require a simulated fouling experiment described above. In this aspect, a parameter which is hereinafter referred as fouling property index (or "FPI") can be determined by relating data on the following properties of a hydrocarbon stream: normal heptane insolubles content (NHI, which is the hydrocarbonaceous materials that are insoluble in n-heptane), solubility blending number ($S_{BN}$), insolubility number ($I_N$), total concentration of metals (i.e., total concentration of Ni and V combined), and total basic nitrogen concentration ([N]). In particular and as disclosed herein, FPI is calculated by:

$$FPI = 2.4 + \frac{NHI}{S_{BN} - I_N} - \{(S_{BN} - I_N) + 1.2 \cdot [\text{Metals}] + [N]\} \quad (3)$$

In the above equation, $S_{BN}$ measures a hydrocarbon's ability to dissolve asphaltenes, while $I_N$ indicates the solvency required to dissolve asphaltenes. For a given oil, the difference between $S_{BN}$ and $I_N$, or $S_{BN}-I_N$, is a measure of the self-compatibility. The determination of $S_{BN}$ and $I_N$ are described in U.S. Pat. No. 5,997,723, e.g., in col. 2, lines 53 to col. 4, line 20, and in U.S. Pat. No. 5,871,634, e.g., in col. 2, line 51 to col. 4, line 25. The disclosure of each of these patents is incorporated by reference herein in its entirety.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Determination of FSI in Accordance with the First Aspect Disclosed Herein

Table 1 shows the properties of five illustrative crude oils that are labeled as Crude 1, Crude 2, Crude 3, Crude 4, and Crude 5.

TABLE 1

Properties of Five Different Crude Oils

| Crude Oil Samples | Crude 1 | Crude 2 | Crude 3 | Crude 4 | Crude 5 |
|---|---|---|---|---|---|
| $S_{BN}$ | 28 | 20 | 38 | 41 | 51 |
| $I_N$ | 27.5 | 9 | 19 | 23 | 24 |
| $S_{BN} - I_N$ | 0.5 | 11 | 19 | 18 | 27 |
| NHI/($S_{BN} - I_N$) | 0.672 | 0.011 | 0.017 | 0.022 | 0.039 |
| API | 38.9 | 44.1 | 39 | 39 | 32.2 |
| TAN | 0.1 | 0.13 | 0.08 | 0.06 | 0.01 |
| Sulfur, wt % | 0.9 | 0.21 | 1.1 | 2.05 | 2.18 |
| Conradson Carbon Residue (CCR) | 2.22 | 1.02 | 1.95 | 3.02 | 3.7 |
| Total N, ppm | 700 | 500 | 408 | 529 | 1200 |
| Basic N, ppm | 135 | 119 | 133 | 163 | 235 |
| ppm Ni + V | 13 | 3 | 4 | 4 | 17 |
| n-heptane asphaltenes, wt % | 0.336 | 0.123 | 0.329 | 0.394 | 1.05 |
| Resid API | 7.9 | 12.7 | 8.0 | 1.0 | 6.1 |
| API/Resid API | 4.9 | 3.5 | 4.9 | 41.1 | 5.3 |
| Naphtha Insolubles | 0.922 | 0.366 | 0.374 | 0.818 | 1.84 |
| Viscosity at 302° F. (cSt) (150° C.) | 0.94 | 1.32 | 0.84 | 0.88 | 1.33 |
| 115-380° F., wt % | 29.58 | 34.83 | 27.6 | 28.19 | 22.12 |
| wt % C | 85.49 | 85.75 | 85.41 | 85.23 | 85.53 |
| wt % H | 14.5 | 14.25 | 14.58 | 14.72 | 14.39 |

TABLE 1-continued

Properties of Five Different Crude Oils

| Crude Oil Samples | Crude 1 | Crude 2 | Crude 3 | Crude 4 | Crude 5 |
|---|---|---|---|---|---|
| 380-650° F. | 29.21 | 27.75 | 29.38 | 27.99 | 27.25 |
| wt % C | 86 | 86.26 | 85.7 | 85.34 | 85.7 |
| wt % H | 13.47 | 13.64 | 13.65 | 13.4 | 13.19 |
| 650-1050° C. | 28.2 | 22.13 | 26.31 | 23.58 | 28.99 |
| wt % C | 85.81 | 86.57 | 85.45 | 84.76 | 85.27 |
| wt % H | 12.43 | 12.92 | 12.61 | 11.55 | 12.38 |
| 1050-1499° C. | 9.29 | 8.51 | 12.7 | 12.25 | 18.87 |

The $\Delta T(t)$ vs. t relationship for these crude oil samples at different rod temperatures was obtained by the procedure described above in the first aspect of the disclosed subject matter, and are presented in FIGS. 3-7. FIGS. 3-7 also show the regression results based on Eq. 2. In addition, the values of k (i.e., FSI) and q at different temperatures of the heated rod were determined and presented in Table 2. As can be seen, at 370° C., the FSI ranking is: Crude 1>Crude 2>Crude 3>Crude 4>Crude 5.

TABLE 2 k and q values five different crude oils at different rod temperatures.

| Crudes | Tc, ° C. | k (FSI) | q | R² |
|---|---|---|---|---|
| Crude 1 | 370 | 0.0324 | 1.440 | 0.9784 |
| Crude 1 | 400 | 0.0396 | 1.326 | 0.9877 |
| Crude 2 | 370 | 0.0083 | 1.813 | 0.9955 |
| Crude 2 | 425 | 0.01823 | 1.663 | 0.9914 |
| Crude 3 | 370 | 0.00687 | 1.672 | 0.9978 |
| Crude 3 | 400 | 0.0287 | 2.306 | 0.9925 |
| Crude 4 | 370 | 0.00557 | 1.262 | 0.9909 |
| Crude 4 | 425 | 0.01203 | 1.101 | 0.9916 |
| Crude 5 | 370 | 0.0025 | 1.229 | 0.9971 |
| Crude 5 | 400 | 0.01085 | 1.754 | 0.9982 |
| Crude 5 | 425 | 0.01626 | 2.203 | 0.9981 |

Example 2

Figure 8:
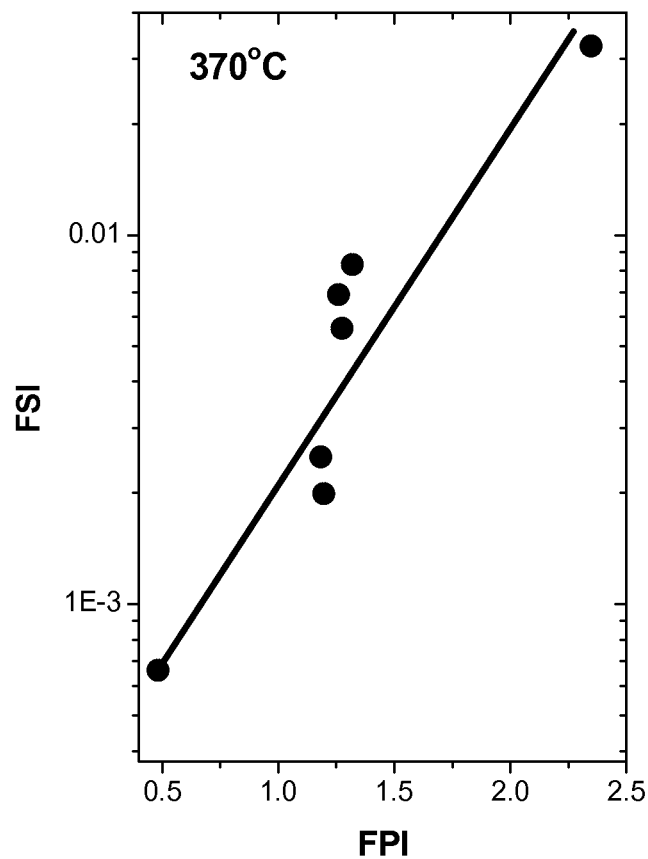
FIG. 8 is a graph displaying the correlation between FSI and FPI at 370° C.
Figure 9:
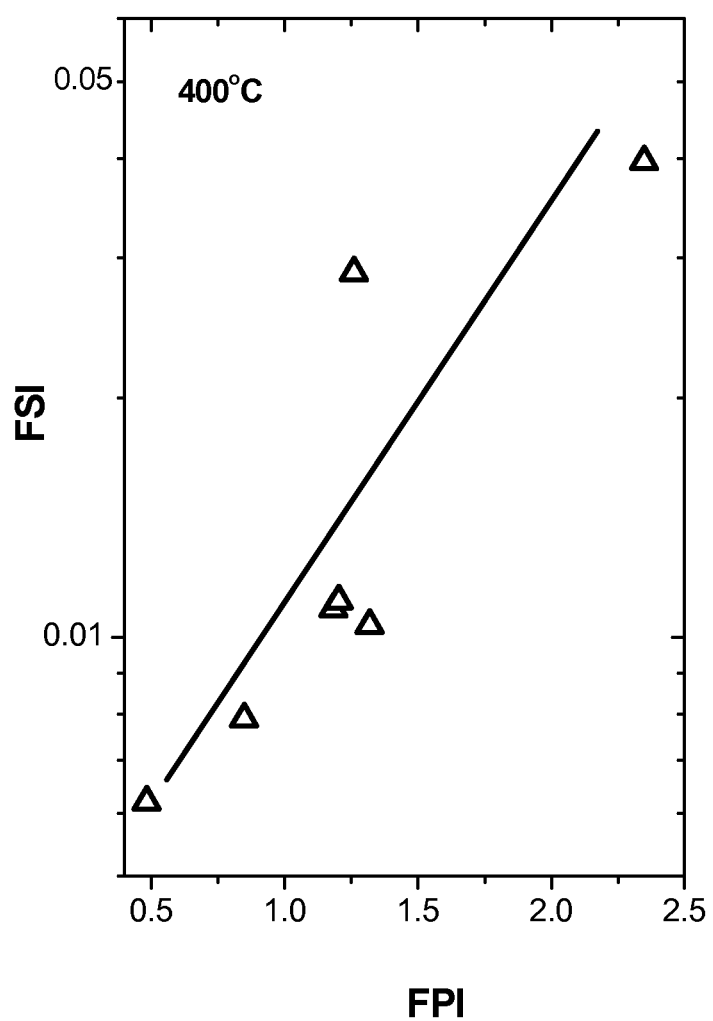
FIG. 9 is a graph displaying the correlation between FSI and FPI at 400° C.
Figure 10:
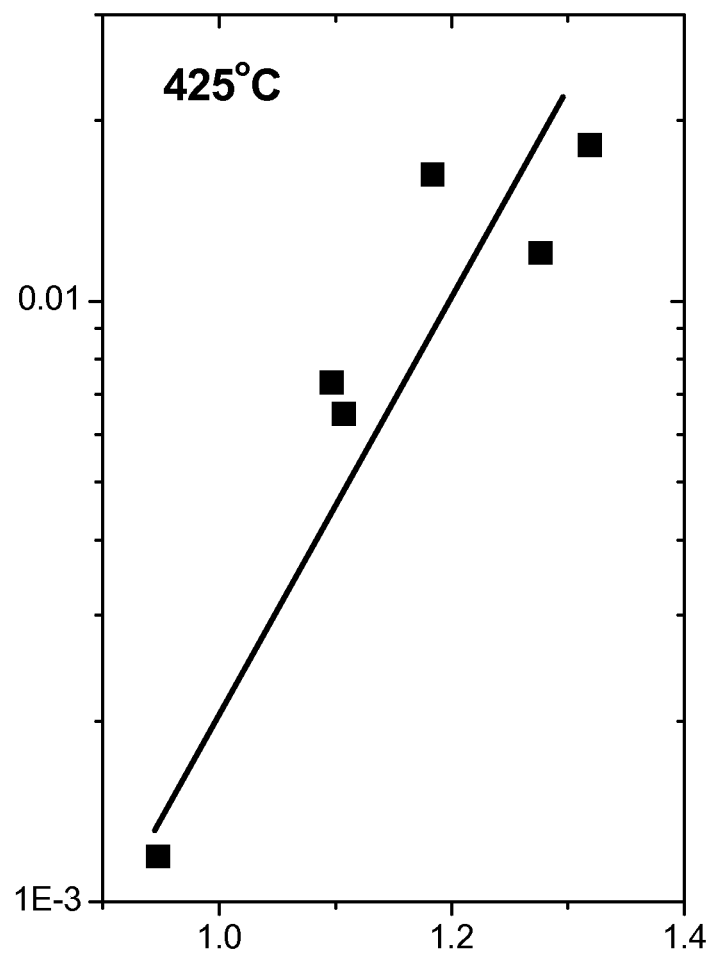
FIG. 10 is a graph displaying the correlation between FSI and FPI at 425° C.

Determination of FPI in Accordance with the Second Aspect Disclosed Subject Matter In accordance with the second aspect of the disclosed subject matter, FPI can be determined based upon Eq. 3 and Table 1 above without performing a simulated fouling test. FPI and FSI are correlated with each other when plotted semi-logarithmically, as can be seen from FIGS. 8-10 for three different temperatures. FIG. 8 illustrates the correlation at 370° C. for seven crude oils, five of which are listed in Tables 1 and 2 (the other two oils are not listed in Tables 1 and 2 for brevity). The FPI correlates with the FSI at three temperatures (370° C., 400° C., and 425° C.), indicating that the FPI is temperature invariant and hence can be used as a fouling property parameter.

In accordance with another aspect of the disclosed subject matter, the FPI and/or FSI parameters can be used for purposes of selecting suitable hydrocarbon streams having a low propensity for fouling for processing in the process equipment. For example, a high FPI or FSI oil (crude or pre-processed) should be purchased at a lower price than a low FPI/FSI oil. In addition, when many oils are blended together to form a mixture, the resulting overall FPI/FSI for the mixture is more important than the FPI/FSI of the individual components. Therefore, in selecting a mixture as the feed stream to a heat exchanger, one should use a mixture with the lowest overall FPI/FSI. Accordingly, the method described above can be used to test oil blends of different compositions to determine whether it is desirable to process such oil blends.

In accordance with another aspect of the disclosed subject matter, the FPI and/or FSI parameters can be used for purposes of determining which hydrocarbon streams may be blended together in order to form a process stream having a lower propensity to foul. For example, different selected crude oils can be blended (in different proportions, if desired) to constitute different oil blends, which are subject to the method of the disclosed to determine their respective FSIs and/or FPIs. Based on the thus-obtained FSIs and/or FPIs, suitable oil blends may be selected, e.g., the ones having the lowest FSI and/or FPI.

The disclosed subject matter is not to be limited in scope by the specific embodiments described herein. Indeed, various modifications to the invention in addition to those described herein will become apparent to those skilled in the art from the foregoing description and the accompanying figures. Such modifications are intended to fall within the scope of the appended claims.

The invention claimed is:

1. A method for determining a propensity of a hydrocarbon stream to foul process equipment, comprising:
   introducing a hydrocarbon stream to a test unit, the test unit comprising a chamber defined by a wall for the hydrocarbon to flow through, an inlet for feeding the hydrocarbon into the chamber, an outlet for discharging the hydrocarbon stream, and a heating element maintained at a substantially constant surface temperature $T_c$ and disposed within the chamber for heating the hydrocarbon flowing across the surface of the heating element to cause fouling;
   obtaining a series of temperature measurements over time of the hydrocarbon stream exiting the outlet of the test unit, including:
      measuring an initial temperature $T_1$ of the hydrocarbon exiting from the outlet when the heating element is essentially free from fouling;
      measuring the temperature $T(t)$ of the hydrocarbon exiting from the outlet successively at predetermined time intervals subsequent to measuring the initial temperature $T_1$, where t denotes time;
   determining a parameter indicative of a propensity of the hydrocarbon to foul process equipment by a regression of $\Delta T(t)$ according to the equation:

$$\Delta T(t) = 1 - \left[ \frac{1 + k(ut/L - 1)}{(1-k)(1 + kut/L)} \right]^{1/(kq)}$$

where $\Delta T(t)$ is a time-dependent quantity which is defined as $\Delta T(t) = (T(t) - T_1)/(T_c - T_1)$, k is the parameter to be determined, t is time, u is the average velocity of the hydrocarbon in the chamber of the test unit, L is the length of the section of the chamber where the hydrocarbon is heated, and q is a factor relating to heat transfer.

2. The method of claim 1, wherein the heating element of the test unit is a heated rod.

3. The method of claim 2, wherein q is a factor relating to heat transfer capacity of the system comprising the test unit wall, the heated rod, and the hydrocarbon stream.

4. The method of claim 2, wherein the constant surface temperature of the heated rod is in a range of from about 300° C. to about 500° C.

5. The method of claim 1, wherein the chamber of the test unit is tubular, and wherein the inlet and the outlet are disposed near the opposing ends of the tubular chamber.

6. The method of claim 1, wherein the hydrocarbon is maintained at a constant predetermined flow rate in the chamber of test unit.

7. The method of claim 1, wherein the hydrocarbon is at least one of a crude oil, a blend of crude oils, or a refinery process stream.

8. A method for reducing fouling of a hydrocarbon stream, comprising obtaining a parameter indicative of the propensity of the hydrocarbon to cause fouling by performing the method of claim 1, determining an effective minimal amount of an antifoulant relative to the amount of hydrocarbon to be processed based on the parameter obtained;

adding the determined amount of the antifoulant to the hydrocarbon to reduce fouling.

9. A method for selecting a first hydrocarbon for blending with at least one second hydrocarbon for the purpose of reduce fouling, comprising obtaining a parameter indicative of the propensity of a mixture of the first hydrocarbon and the at least one second hydrocarbon to cause fouling by performing the method of claim 1, and based on the parameter obtained, determining whether to select the first hydrocarbon to blend with the at least one second hydrocarbon for reduce fouling.

10. A method for selecting crude oils to form a suitable oil blend for processing in for the purpose of reduce fouling, comprising forming a plurality of oil blends by mixing at least two different crude oils;

obtaining a parameter indicative of the propensity of each of the oil blends to cause fouling by performing the method of claim 1; and selecting at least one oil blend for processing based on the obtained parameter of the oil blend.

11. A method for determining whether to purchase a hydrocarbon, comprising obtaining a parameter indicative of the propensity of the hydrocarbon to cause fouling by performing the method of claim 1, and based on the parameter obtained, determining whether to purchase the hydrocarbon.

\* \* \* \* \*